United States Patent [19]

Takeoka

[11] Patent Number: 5,352,816

[45] Date of Patent: Oct. 4, 1994

[54] ORGANOSILICON COMPOUND

[75] Inventor: Toru Takeoka, Cincinnati, Ohio

[73] Assignee: Three Bond Co., Ltd., Tokyo, Japan

[21] Appl. No.: 174,238

[22] Filed: Dec. 28, 1993

[51] Int. Cl.$^5$ ............................................. C07F 7/10
[52] U.S. Cl. ................................................. 556/420
[58] Field of Search ...................................... 556/420

[56] References Cited

U.S. PATENT DOCUMENTS

| | | | |
|---|---|---|---|
| 3,962,160 | 6/1976 | Beers et al. | 260/18 S |
| 4,213,914 | 7/1980 | Bargain et al. | 556/420 X |
| 4,323,489 | 4/1982 | Beers | 524/788 |
| 4,861,908 | 8/1989 | Satoh et al. | 556/420 |
| 5,070,215 | 12/1991 | Bambury et al. | 556/420 X |
| 5,194,646 | 3/1993 | Yamada et al. | 556/420 |
| 5,208,312 | 5/1993 | Boutevin et al. | 556/420 X |
| 5,256,706 | 10/1993 | Carpenter et al. | 556/420 X |

*Primary Examiner*—Paul F. Shaver
*Attorney, Agent, or Firm*—Scully, Scott, Murphy & Presser

[57] ABSTRACT

Disclosed is an organosilicon compound represented by the general formula

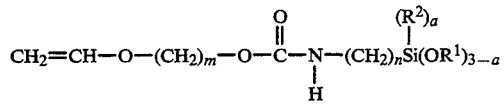

wherein m and n are each an integer of 1 to 5, $R^1$ and $R^2$ are each independently an alkyl group having 1 to 3 carbon atoms or allyl, and a is an integer of 0 to 2. This organosilicon compound is a novel compound capable of affording a photopolymerizable organopolysiloxane of high quality.

2 Claims, 1 Drawing Sheet

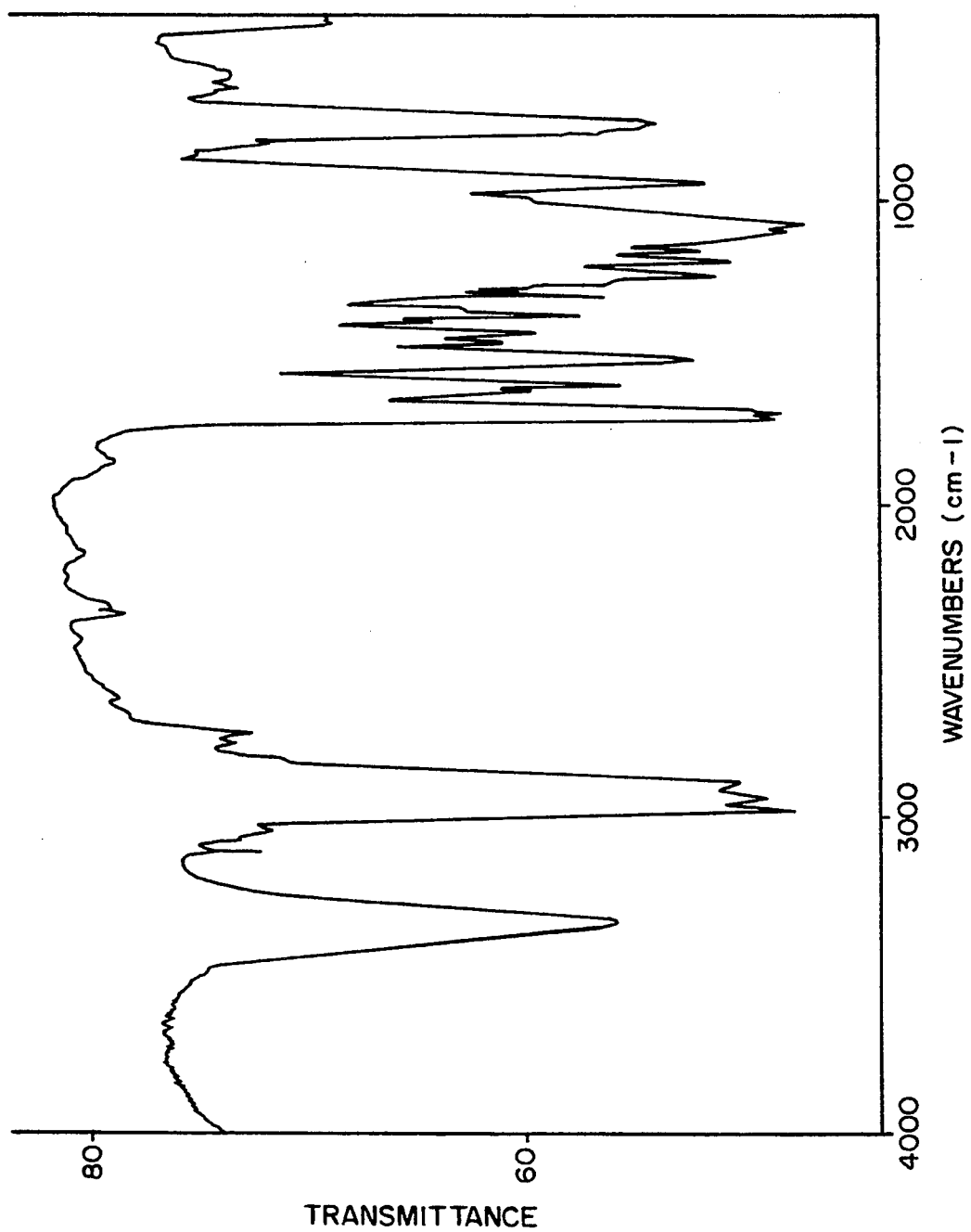

ORGANOSILICON COMPOUND

BACKGROUND OF THE INVENTION

The present invention relates to a novel organosilicon compound, particularly an organosilicon compound having vinyl ether group and an alkoxy group attached directed to silicon atom which compound is useful as an intermediate material for potting, sealing, coating, etc. of electric and electronic parts, as well as a process for preparing such organosilicon compound.

Photocurable silicone composition have heretofore been used for potting, sealing, coating, etc. of electric and electronic parts. However, the photocurable silicone compositions which are presently known involve problems: for example, a photocuring reaction does not always proceed at a sufficiently high speed, or their curing mechanism is apt to be impaired by the oxygen in air. Further, in a shaded place where light such as ultraviolet light cannot reach, there remains an uncured portion.

Having made studies for obtaining a novel photocurable organopolysiloxane composition free of the above-mentioned problems of the prior art, the present inventors found out an intermediate affording an organopolysiloxane which is cured by both a moisture-curing mechanism and a photocuring mechanism. Accordingly, it is the object of the present invention to provide a novel silicon compound capable of affording an cyanopolysiloxane useful in the foregoing uses.

SUMMARY OF THE INVENTION

The organosilicon compound of the present invention is an organoxilane represented by the following general formula:

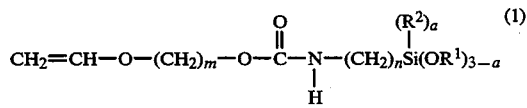
(1)

where $R^1$ and $R^2$ are each independently an alkyl group having 1 to 3 carbon atoms or allyl, a is an integer of to 2, m and n are each an integer of 1 to 5.

The following compound is mentioned as a concrete example:

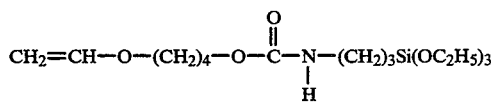

The organosilicon compound of the present invention can be prepared easily by a condensation reaction of a vinyl ether represented by the following general formula, containing hydroxyl group as an end group:

$$CH_2=CH-O-(CH_2)_m-OH \quad (2)$$

with a silane compound represented by the following general formula, containing isocyanate group as an end group:

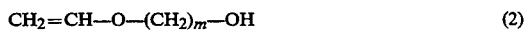
(3)

Usually, the reaction is carried out at an ambient temperature in an inert atmosphere such a nitrogen and in the presence of an organometallic catalyst, e.g. dibutyltin dilaurate.

The following is a general reaction formula:

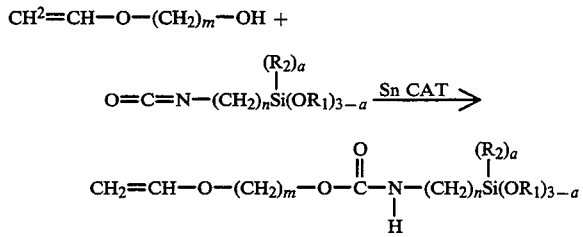

The organosilicon compound of the general formula (1) according to the present invention is a novel compound not reported in any literature yet. This compound can be applied to various uses. For example, this compound has an end vinyl ether group which possesses cationic photopolymerizability, and also has an end alkoxy group on the opposite end, thus having a double curing performance of both photopolymerizability and condensation-polymerizability. Because of such a double curing performance, this compound can exhibit a satisfactory curing performance .even in a shaded place where light does not reach. Also this compound can be used for introducing a vinyl ether group into a monomer or oligomer having an end hydroxy group by utilizing the reactivity of the end alkoxysilyl group and thus the synthesis of a cationic photopolymerizable monomer of oligomer can be done easily. For example, by reacting this compound with an organosiloxane having an end hydroxyl group, it is made possible to obtain a photopolymerizable silicone easily. Further, by using a compound having two or more alkoxysilyl groups, it is made possible to introduce both cationic photopolymerizability and moisture-polycondensability into a monomer or oligomer. Thus, various curable resin compounds can be prepared using the organosilicon compound of the present invention as a starting material. These compounds are considered to be particularly useful as potting, sealing and coating materials for electric and electronic parts.

BRIEF DESCRIPTION OF THE DRAWING

FIG. 1 shows an infrared absorption spectrum of the product obtained in the working Example.

A working example of the present invention will be described below.

EXAMPLE 116 g of hydroxybutyl vinyl ether (RAPI-CURE HBVE MONOMER, a product of GAF CHEMICALS CORPORATION) and 247 g of isocyanatopropyltriethoxysilane (A-1310, a product of UNION CARBIDE CORP.) were placed in a reactor, and after purging the interior of the reactor with nitrogen gas, 0.05 g of dibutyltin dilaurate was dropwise added slowly with stirring. Thereafter, the reaction solution temperature rose in several minutes and up to 60° C. in about 30 minutes. Thereafter, in about 3 hours, the reaction temperature began to drop gradually, and after 6 hours, it dropped to room temperature.

After the end of the reaction, the product obtained was subjected to FT-IR analysis to make sure that it was the following object product (see Chart ①):

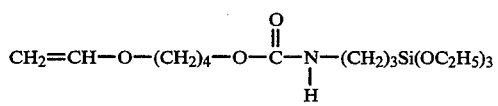

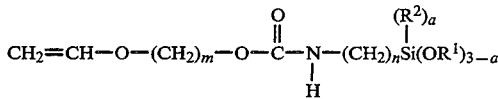

Further, for confirming the photocuring performance of the vinyl ether group, 0.5 g of allylphenyl-iodium-hexafluoroantimonate salt (UV-9310C, a product of GE Co.) was added as a cat ionic polymerization initiator to 50 g of the product (4), followed by mixing under stirring. This composition was then applied onto an iron plate having a width of 50 mm, a length of 50 mm and a thickness of 1 mm to a thickness of about 0.1–0.5 mm, and ultraviolet light was radiated to the thus-coated iron plate for 30 seconds using a high-pressure mercury vapor lamp having an illuminance of 100 mw/cm². As a result, the composition was cured into an elastomeric film.

What is claimed is:

1. An organosilicon compound represented by the following general formula:

wherein m and n are each an integer of 1 to 5, $R^1$ and $R^2$ are each independently an alkyl group having 1 to 3 carbon atoms or allyl, and a is an integer of 0 to 2.

2. A process for preparing an organosilicon compound represented by the general formula described in claim 1, which process is characterized by a condensation reaction of a vinyl ether containing an end hydroxyl group and represented by the general formula

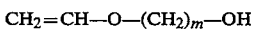

with a silane compound containing an end isocyanate group and represented by the general formula

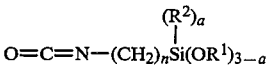

in which formulae $R^1$, $R^2$a, m and n are as defined in claim 1.

* * * * *

UNITED STATES PATENT AND TRADEMARK OFFICE
CERTIFICATE OF CORRECTION

PATENT NO. : 5,352,816
DATED : October 4, 1994
INVENTOR(S) : Toru Takeoka

It is certified that error appears in the above-indentified patent and that said Letters Patent is hereby corrected as shown below:

Column 1, line 31: "cyanopolysiloxane" should read --organopolysiloxane--

Column 1, line 44: after "of" insert --O--

Column 4, line 25, Claim 1: "$R^2a,$" should read --$R^2$, a,--

Signed and Sealed this

Fourth Day of July, 1995

Attest:

BRUCE LEHMAN

Attesting Officer          Commissioner of Patents and Trademarks